United States Patent [19]

Lovell

[11] 4,087,525
[45] May 2, 1978

[54] PENTADIENONE HYDRAZONES AS INSECTICIDES

[75] Inventor: James Byron Lovell, Pennington, N.J.

[73] Assignee: American Cyanamid Company, Stamford, Conn.

[21] Appl. No.: 793,117

[22] Filed: May 2, 1977

Related U.S. Application Data

[63] Continuation-in-part of Ser. No. 638,252, Dec. 8, 1975, abandoned.

[51] Int. Cl.² .......................... A01N 9/20; A01N 9/22
[52] U.S. Cl. ..................................... 424/244; 424/251; 424/273 R; 424/327
[58] Field of Search ............... 424/244, 251, 273, 327

[56] References Cited

U.S. PATENT DOCUMENTS 3,878,201   4/1975   Tomcufcik ...................... 260/240 G

*Primary Examiner*—Allen J. Robinson
*Attorney, Agent, or Firm*—H. G. Jackson

[57] ABSTRACT

The invention relates to a method for controlling insects by contacting the insects, and/or applying to their habitat or food supply, with an insecticidally effective amount of a compound of the formula:

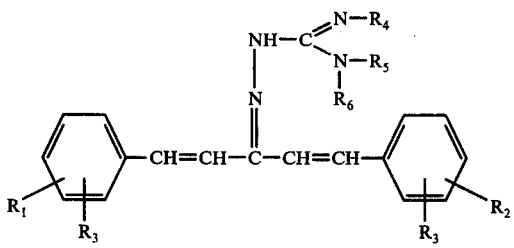

wherein $R_1$ and $R_2$ each represent hydrogen, halogen, $CF_3$, $C_1$-$C_4$ alkyl, $C_1$-$C_4$ alkoxy or $C_1$-$C_4$ alkylthio; $R_3$ is hydrogen or methyl, provided that when $R_3$ is methyl, $R_1$ and $R_2$ are also methyl; $R_4$ and $R_5$ represent hydrogen or $C_1$-$C_4$ alkyl, and when taken together, an alkylene group of 2 to 6 carbon atoms, methyl or a phenyl alkylene group of 2 to 4 carbon atoms, a dimethyl alkylene group of 2 to 4 carbon atoms or 1,2-cyclohexylene; and $R_6$ is hydrogen or $C_1$-$C_4$ alkyl; and salts thereof.

25 Claims, No Drawings

PENTADIENONE HYDRAZONES AS INSECTICIDES

This application is a continuation-in-part of application Ser. No. 638,252 filed Dec. 8, 1975 now abandoned.

The invention pertains to insect control by a chemical method. Certain pentadien-3-one substituted amidino hydrazones are described in U.S. Pat. No. 3,878,201 (1975). The patentee describes a method for the manufacture of a wide variety of such hydrazones and salts thereof and indicates that the compounds are effective as anti-malarial and anti-tubercular agents for warm-blooded animals. There is, however, no suggestion that the compounds are useful as insecticidal agents.

The invention relates to a method for controlling insects, particularly Lepidopterous insects, Orthopterous insects, Dipterous insects and Hymenopterous insects by contacting the insects, and/or applying to their habitat or food supply, with an insecticidally effective amount of a pentadienone hydrazone having the structure:

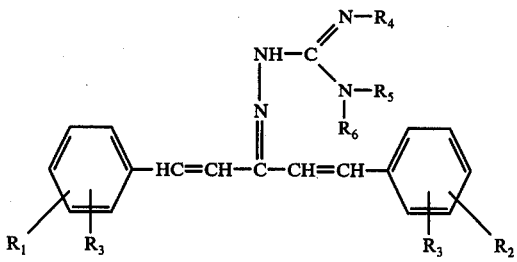

wherein $R_1$ and $R_2$ each represent hydrogen, halogen, $CF_3$, $C_1$-$C_4$ alkyl, $C_1$-$C_4$ alkoxy or $C_1$-$C_4$ alkylthio; $R_3$ is hydrogen or methyl, provided that when $R_3$ is methyl, $R_1$ and $R_2$ are also methyl, $R_4$ and $R_5$ represent hydrogen or $C_1$-$C_4$ alkyl, and when taken together, an alkylene group of 2 to 6 carbon atoms, methyl or phenyl alkylene group of 2 to 4 carbon atoms, a dimethyl alkylene group of 2 to 4 carbon atoms or 1,2-cyclohexylene; and $R_6$ is hydrogen or $C_1$-$C_4$ alkyl; and salts thereof. The invention also relates to a method for protecting agronomic crops, trees, shrubs, ornamentals, and the like, from attack by insects, by applying to the crops an insecticidally effective amount of a compound having the above structure.

The term "halogen" as used herein, is intended to mean chloro, fluoro, bromo and iodo. However, chloro and bromo are preferred.

Preferred compounds for use as insecticidal agents and as protecting agents for crops have the above structure, wherein $R_1$ and $R_2$ represent the same substituent, and the substituent is H, Cl, Br, $CF_3$, $C_1$-$C_3$ alkyl, methoxy or methylthio; $R_3$ is hydrogen; $R_4$ and $R_5$ each represent hydrogen, $C_1$-$C_3$ alkyl, $C_2$-$C_6$ alkylene, or methyl, dimethyl, or phenyl $C_2$-$C_4$ alkylene; $R_6$ is hydrogen; and the acid addition salts thereof, preferably the hydrochloride, hydrobromide or hydriodide.

Still more preferred are compounds as described above, where $R_1$ and $R_2$ are each p-chloro or each p-$CF_3$; $R_3$ and $R_6$ are each hydrogen; and $R_4$ and $R_5$ are taken together and are $C_2$-$C_6$ alkylene or methyl, dimethyl or phenyl $C_2$-$C_4$ alkylene; $R_6$ is hydrogen; and the acid addition salts thereof, preferably the hydrochloride, hydrobromide or hydriodide.

Still more preferred are compounds as described above, where $R_1$ and $R_2$ are each p-chloro or each p-$CF_3$; $R_3$ and $R_6$ are each hydrogen; and $R_4$ and $R_5$ are taken together and are $C_2$-$C_6$ alkylene or methyl, dimethyl or phenyl $C_2$-$C_4$ alkylene; and the acid addition salts thereof.

In accordance with this invention, I have found that control of insects, particularly Lepidopterous insects, Orthopterous insects, Dipterous insects and Hymenopterous insects and protection of agronomic crops, trees, shrubs and ornamentals, from attack by the insects, can be achieved by the application of an insecticidally effective amount of a pentadienone hydrazone to the crops or to the habitat or food supply of the insects. In practice, generally about 0.28 kg/hectare, 11.2 kg/hectare, and preferably 0.56 kg/hectare to 4.8 kg/hectare of the pentadienone hydrazone is effective for insect control and/or for crop protection.

The hydrazones of this invention can be applied in either liquid or solid form. They may be applied in solid form as dusts or dust concentrates, or in liquid for as emulsifiable concentrates, flowable liquids or wettable powders which are dispersed in water or other inexpensive liquid for application as a finely divided spray.

A typical emulsifiable concentrate can be prepared by admixing from about 12% to 29% by weight of the pentadienone hydrazone, about 8% to 12% by weight of a blend of nonionic emulsifiers such as T-Mulz 339 (sold by Thompson-Hayward of Kansas City, Kansas), or polyoxyethylene derivatives and blends with alkyl aryl sulfonates, and about 59% to 80% by weight of cyclohexanone or a heavy aromatic solvent having a mixed aniline between 30° F. and 95° F., a specific gravity between 0.880 and 1.5 at 60°/60° F., and an aromatic content of 60% to 100%. These formulations provide from 119.8 g/liter to 239.6 g/liter of the active hydrazone, and are generally diluted with water for application as a dilute liquid. However, said formulations can also be applied in the form of undiluted discrete droplets as low volume or ultra-low volume sprays. For such application, the emulsifiable concentrate is usually applied with apparatus designed to disperse the liquid in the form of finely divided discrete droplets having a mass median diameter of from 25 to 150 microns.

A typical wettable powder formulation can be prepared by grinding together about 34% by weight of a synthetic calcium silicate, 12% by weight of a dispersing agent such as sodium lignosulfonate, 4% by weight of a wetting agent such as an alkyl aryl sulfonate, and 50% by weight of the pentadienone hydrazone. Such formulation is generally dispersed in water for application as a liquid spray.

I have found that pentadienone hydrazones, as represented by the formula set forth above, are useful for the control of insects, especially a wide variety of Lepidopterous insects, Orthopterous insects, Dipterous insects and Hymenopterous insects.

The pentadienone hydrazones of this invention are highly effective for controlling insects of the orders Orthoptera and Diptera and especially active and very selective against Lepidopterous larvae such as southern armyworms [*Spodoptera eridania* (Cramer)], cabbage loopers [*Trichoplusia ni* (Hübner)], tobacco budworms [*Heliothis virescens* (Fabricus)], gypsy moth [*Porthetria dispar* (L.)], and the like, at 10 to 1000 ppm rates. they do not appear to be especially toxic to most beneficial insects, and thus are useful for pest management and integrated control programs. Additionally, I have found that the above-identified compounds exhibit relatively low mammalian toxicity when ingested, and are only slightly irritating when introduced directly into the eye of a rabbit. Moreover, these compounds show virtually no phytotoxicity to plants at rates of application up to 11.2 kg/hectare.

Advantageously, the pentadien-3-one hydrazone compounds of this invention are active as stomach poisons thus are effective against insects with chewing mouth parts as well as those with sponge and lapping mouth parts. They are especially effective for the control of ants, Family Formicidae, and may be used for the control of fire ants such as the southern fire ant, *Solenopsis xyloni,* (xyloni,) leaf-cutting ants *ACROMYRMEX versicolor* (Pergande), Argentine ants *IRIDOMYRMEX humilis (Mayr), black carpenter ants, CAMPONOTUS pennsylvanica* (DeGeer), cornfield ants *LASIUS alienus (Foerster), pavement ants TETRAMORIUM caespitum,* larger yellow ants ACANTHOMYOPS interjectus (Mayr), thief ants *SOLENOPSIS molesta* (Say), and the red imported fire ant *Solenopsis invicta* Bruen, and the black imported fire ant, *Solenopsis saevissima richteri.* These ants are serious economic pests generally found in the warmer climates such as the subtropical and tropical zones. They feed on seeds and tender stems of young plants and are responsible, annually, for substantial damage to agronomic crops. They have likewise been known to attack humans, nesting birds, livestock, poultry and household pets. As such, it is most desirable to control these economic pests.

Control of these pests can be achieved with treated baits that are distributed in the crop area, pasture, park or other location in which ant control is desired, and made available to worker ants. The workers carry the treated bait to the colony where it is consumed by the queens and the young ants, thus leading to their destruction.

Baits can be prepared, for example, by admixing the pentadienone hydrazone with peanut butter, citrus pulp, apple pumice, wheat-bran, corn meal-sugar, and vegetable oils such as soybean oil and distributed as is; or these compositions can be placed in soda straws on carriers such as corn cob grits, clays, pumice, synthetic polymer compositions or the like and distributed in the area of the colony. Use of these baits has particular advantage, since such method of distribution poses little or no hazard to animals that may frequent the crop area.

These and other advantages will become apparent from the examples provided below.

EXAMPLE 1

The insecticidal activity of the compounds of this invention is demonstrated by the following tests, wherein pentadienone hydrazones are evaluated against test insect species at rates of from 10 to 1000 ppm. Test formulations and procedures used for evaluation are as follows:

Test Formulations.
  A. 100 mg of the test material is weighed, placed in a funnel over a 113 g narrow-mouth bottle, and rinsed into the bottle with a 35 ml scoop of acetone, followed by a scoop of water and another scoop of acetone to yield 1000 ppm in 65% acetone. If the material is not soluble, it is broken up with a glass rod and used as a suspension.
  B. This stock solution ("A") is used to make 300 ppm solutions or suspensions by pipetting 30 ml of "A" into a bottle containing 70 ml of 50% acetone to yield 300 ppm. Further dilutions in 50% acetone are made as required.
  C. Tests requiring 10 ppm acetone solutions: 1 ml of "A" is pipetted into 99 ml of acetone to yield 10 ppm. Additional dilutions are made using 50% acetone as required.

Initial Tests

Tobacco Budworm - *Heliothis virescens* (Fabricus).

A cotton plant with 2 true leaves expanded is dipped for 3 seconds with agitation in 300 ppm solution. A 1.27 to 1.91 cm square of cheesecloth with about 50 to 100 budworm eggs 0–24 hours old is also dipped in the test solution and placed on a leaf of the cotton plant, all being placed in the hood to dry. The leaf with the treated budworm eggs is removed from the plant and placed in a 226 g Dixie cup with a wet 5 cm piece of dental wick and covered with a lid. The other leaf is placed in a similar cup with a wick and a piece of cheesecloth infested with 50–100 newly hatched larvae is added before covering the cup with a lid. After 3 days at 80° F., 50% r.h., observations of egg hatch are made, as well as kill of newly hatched larvae, any inhibition of feeding, or interference of any sort with normal development.

Southern Armyworm - *Spodoptera eridania* (Cramer).

A Sieva lima bean plant with just the primary leaves expanded to 1.91 cm is dipped for 3 seconds with agitation in the "A" solution of 1000 ppm and set in the hood to dry. Following this, one leaf is placed in a 9 cm petri dish which has a moist filter paper in the bottom and 10 third-instar armyworm larvae about 1 cm long. This dish is covered and held at 80° F., and 50% r.h. After 2 days, mortality counts and estimates of the amount of feeding are made. Compounds showing partial kill and/or inhibition of feeding are held for an extra day for further observations. Those materials which produce greater than 75% mortality, or which show only trace feeding damage are further tested.

All compounds showing activity as defined above are retested, using the second leaf on the bean plant, after an interval of 7 days from original treatment, as an assay of residual activity.

Secondary Tests.

Tobacco Budworm - *Heliothis virescens* (Fabricus) Third Instar.

Three cotton plants with just expanded cotyledons are dipped in 1000 ppm solution and placed in the hood to dry. When dry, each cotyledon is cut in half, and 10 are each placed in a 28 g plastic medicine cup containing a 1.25 cm dental wick saturated with water and one third-instar budworm larva is added. The cup is capped and held for 3 days at 80° F 50% r.h., after which morality counts are made. Compounds killing more than 75% of the larvae are further tested.

Cabbage Looper - *Trichoplusia ni* (Hubner) - Third Instar.

A true leaf of a cotton plant is dipped into the test solution, agitated for 3 seconds, and removed to dry in an exhaust hood. When dry, the leaf is placed in a 9.0 cm petri dish with moist filter paper on the bottom. Ten third-instar larvae are added the lid placed on the dish. Mortality counts are made after 3 days at 80° F and 50 + 10% r.h. Compounds killing more than 75% of the loopers are further tested.

Data obtained are reported in Table I below.

TABLE I

Evaluation of Pentadienone Hydrazones as Insecticides

| Compound | Budworm Eggs 300 ppm | Budworm Eggs 100 ppm | Budworm Eggs 10 ppm | Budworm Larvae 300 ppm | Budworm Larvae 100 ppm | Budworm Larvae 10 ppm | Armyworms 1000 ppm | Armyworms 100 ppm | Armyworms 10 ppm | Armyworms 7 Days | Tobacco Budworm 1000 ppm | Tobacco Budworm 100 ppm | Cabbage Looper 1000 ppm | Cabbage Looper 100 ppm |
|---|---|---|---|---|---|---|---|---|---|---|---|---|---|---|
| 1,5-bis($\alpha,\alpha,\alpha$-Trifluoro-p-tolyl)-1,4-pentadien-3-one, 4,5,6,7-tetrahydro-1H-1,3-diazepin-2-ylhydrazone | 0 | | | 100 | 100 | 100 | 100 | 100 | 100 | 100* | 100 | 100 | 100 | 100 |
| 1,5-bis($\alpha,\alpha,\alpha$-Trifluoro-p-tolyl)-1,4-pentadien-3-one, 4,5,6,7-tetrahydro-1H-1,3-diazepin-2-ylhydrazone hydrochloride | 0 | | | 100 100 | 100 100 | 90 0 0 | 100 | 100 | 100 | 100* 100** | 100 | 100 | 100 | 100 |
| 1,5-bis(p-Chlorophenyl)-1,4-pentadien-3-one, 4,5,6,7-tetrahydro-1H-1,3-diazepin-2-ylhydrazone hydriodide | 0 | | | 100 | | | 100 | 100 | | 100* 100** | 40 R | 0 R | 100 | |
| 1,5-bis(p-Chlorophenyl)-1,4-pentadien-3-one 4-phenyl-2-imidazolin-2-ylhydrazone | 0 | | | 100 | 100 90 | 0 | 100 | 100 | 0 | 100* 100** | 100 | 80 60 | 100 | 70 |
| 1,5-bis(p-Chlorophenyl)-1,4-pentadien-3-one, 4-phenyl-2-imidazolin-2-ylhydrazone hydriodide | 0 | | | 100 | 100 | 0 | 100 | 100 | 0 | 100* 100** | 80 | 30 | 100 | 100 |
| 1,5-bis(p-Chlorophenyl)-1,4-pentadien-3-one, 4,4-dimethyl-2-imidazolin-2-ylhydrazone | | | | 100 | 90 | | 100 | 100 | | 100* 100** | 30 R | 10 R | 100 | |
| 1,5-bis(p-Chlorophenyl)-1,4-pentadien-3-one, 4-methyl-2-imidazolin-2-ylhydrazone hydrochloride | — | 0 | | 100 | 90 100 | 0 | 100 | 100 90 | 0 | 100* 50** | 0 R | 0 | 100 | 0 |
| 1,5-bis(p-Chlorophenyl)-1,4-pentadien-3-one, 3$\alpha$,4,5,6,7,7a-hexahydrobenzimidazol-2-ylhydrazone hydrobromide | 0 | | | 100 | 100 | 0 | 100 | 100 | 0 | 100* 100** | 50 | 0 R | 100 | 80 |
| 1,5-bis(p-Chlorophenyl)-1,4-pentadien-3-one, 1,4,5,6-tetrahydro-5,5-dimethyl-2-pyrimidinylhydrazone hydrobromide | 0 | | | 100 | 100 | 0 | 100 | 100 | 60 | 100* 100** | 90 | 60 50 | 100 | 10 |
| 1,5-bis(p-Chlorophenyl)-1,4-pentadien-3-one, 1,4,5,6,7,8-hexahydro-1,3-diazocin-2-ylhydrazone, hydrochloride | 0 | | | 90 | 50 | 0 | 100 | 100 | 0 | 100* 60** | 0 | 0 R | 100 | 10 |
| 1,5-bis(p-Chlorophenyl)-1,4-pentadien-3-one, 1,4,5,6-tetrahydropyrimidin-2-ylhydrazone hydriodide | 0 | | | 0 | | | 100 | 0 | 0 | 0* | 60 | | 0 | |
| 1,5-bis(p-Chlorophenyl)-1,4-pentadien-3-one, 2-imidazolin-2-ylhydrazone hydrobromide with methanol | 0 | | | 50 | 0 | | 100 | 60 | | 100* | 0 R | 0 | 40 R | 0 |
| 1,5-bis(p-Isopropylphenyl)-1,4-pentadien-3-one, 2-imidazolin-2-ylhydrazone hydrobromide | 0 | | | 0 | | | 100 | 10 | | 100* | 20 R | 0 | 80 | |
| 1,5-di(p-Cumenyl)-1,4-pentodien-3-one, 2-imidazolin-2-ylhydrazone hydrobromide | 0 | | | 0 | | | 100 | 10 | | 100* | 0 | 0 | 20 R | |
| 3-{[p-Isopropyl-$\alpha$-(p-isopropylstyryl)cinnamylidene]amino}-1,1-dimethylguanidine hydriodide | | | | 0 R | 0 | | 100 | 40 | | 0* 0** | 0 R | 0 | 0 R | |
| 1,5-bis(p-Chlorophenyl)-1,4-pentadien-3-one, 1,4,5,6-tetrahydro-2-pyrimidinylhydrazone hydrochloride with methanol | | | | 50 | 0 | | 100 | 90 60 | 0 | 100* 20** | 0 R | 0 | 0 R | 0 |
| 1,5-bis(p-Chlorophenyl)-1,4-pentadien-3-one, 4,5,6,7-tetrahydro-1H-1,3-diazepin-2-ylhydrazone hydrochloride | 0 | | | 100 | 0 | 0 | 100 | 100 | 0 | 100* | 70 | | 0 | |
| 1,5-bis[p-(methylthio)phenyl]-1,4-pentadien-3-one, 4,5,6,7-tetrahydro-1H-1,3-diazepin-2-ylhydrazone with benzene | 0 | | | 0 | | | 100 | 80 | 0 | 40* | 0 | | 0 | |
| 1,5-di-p-Cumenyl-1,4-pentadien-3-one, 4,5,6,7-tetrahydro-1H-1,3-diazepin-2-ylhydrazone | | | | 0 | 0 | | 100 | 0 | | 100* | 20 R | 10 | 100 | 0 |
| 1-{[p-Chloro-$\alpha$-(p-chlorostyryl)cinnamylidene]amino}-2,3-diisopropyl hydroiodide | 0 | | | 75 | 0 | | 100 | 0 | | 100* | 0 R | 0 | 80 | 0 |
| 1-(p-Chlorophenyl)-5-p-tolyl-1,4-pentadien-3-one, 2-imidazolin-2-ylhydrazone hydro- | 0 | | | 0 | | | 100 | 20 | | 100* | 0 R | 30 0 R | 20 R | 0 |

TABLE I-continued

Evaluation of Pentadienone Hydrazones as Insecticides

| Compound | Budworm Eggs 300 ppm | Budworm Eggs 100 ppm | Budworm Eggs 10 ppm | Budworm Larvae 300 ppm | Budworm Larvae 100 ppm | Budworm Larvae 10 ppm | Armyworms 1000 ppm | Armyworms 100 ppm | Armyworms 10 ppm | Armyworms 7 Days | Tobacco Budworm 1000 ppm | Tobacco Budworm 100 ppm | Cabbage Looper 1000 ppm | Cabbage Looper 100 ppm |
|---|---|---|---|---|---|---|---|---|---|---|---|---|---|---|
| bromide with ethyl alcohol | | | | | | | | | | | | | | |
| 1,5-bis(p-Bromophenyl)-1,4-pentadien-3-one, 2-imidazolin-2-ylhydrazone hydrobromide with propyl alcohol | 0 | 0 | 0 | 100 100 | 100 | 0 | 100 100 | 90 | 0 | 70* 0** | 0 | — | | |
| 1,5-bis(α,α,α-Trifluoro-p-tolyl)-1,4-pentadien-3-one, 2-imidazolin-2-ylhydrazone hydrobromide | 0 | | | 100 | 0 | 0 | 100 | 40 | 0 | 100* | 70 | | 0 | |
| 1,5-bis(p-Bromophenyl)-1,4-pentadien-3-one, 2-imidazolin-2-ylhydrazone hydrobromide | 0 | | | 0 | | | 100 | 60 | | 100* | 30 R | 0 R | 0 R | 0 |
| 1,5-di-3,5-Xylyl-1,4-pentadien-3-one, 4,5,6,7-tetrahydro-1H-1,3-diazepin-2-ylhydrazone hydrochloride | 0 | | | 0 | | | 100 | 0 | | 0* | 0 | | 0 | |
| 1,5-bis(p-Chlorophenyl)-1,4-pentadien-3-one, 1-methyl-2-imidazolin-2-ylhydrazone hydroiodide | 0 | | | 50 | 0 | | 100 | 0 | | 100* | 20 R | 0 R | 0 R | 0 |
| 1,5-bis(p-Chlorophenyl)-1,4-pentadien-3-one, N,N'-diethylamidinohydrazone hydriodide | 0 | | | 75 | 0 | | 100 | 60 | | 100* 0** | 0 R | 0 R | 40 R | 0 |
| (α-Styrylcinnamylideneamino)-guanidine hydrochloride | 0 | | | 0 | | | 100 100 | 0 | | 0* | 0 | | 0 | — |
| 1,5-bis(p-Chlorophenyl)-1,4-pentadien-3-one, 2-imidazolin-2-ylhydrazone hydrochloride | | | | 50 | 0 | | 100 | 70 60 | 0 | 100* 30** | 0 | 0 | 0 R | 0 |
| [(p-Methoxy-α-(p-methoxystyryl)cinnamylidene)amino]-guanidine hydrochloride | 0 | | | 0 | | | 100 0 R | 0 | 0 | 0* | 30 R | 0 | 0 | 0 |
| {[o-Chloro-α-(o-chlorostyryl)cinnamylidene]amino}-guanidine hydrochloride | 0 | | | 0 | | | 90 100 | 0 | | | | | | |
| {[p-Chloro-α-(p-chlorostyryl)cinnamylidene]amino}-guanidine hydrochloride | | | | | | | 100 | 0 | | | 0 | | | |
| 1,5-bis(m-Chlorophenyl)-1,4-pentadien-3-one, 2-imidazolin-2-ylhydrazone hydrobromide | | | | | | | 100 | | | | | | | |
| 1,5-bis(p-Chlorophenyl)-1,4-pentadien-3-one, 1,4,5,6-tetrahydro-5,5-dimethyl-1,2-pyrimidinylhydrazone | 0 | | | 100 | 0 | | 100 | 100 | 100 | 100* 100** | 100 | 100 | 100 | 100 |
| 1,5-bis(p-Chlorophenyl)-1,4-pentadien-3-one, 1,4,5,6-tetrahydro-5,5-dimethyl-1,2-pyrimidinylhydrazone, hydrochloride, compound with ethanol | 0 | | | 90 | 0 R | | 100 | 100 | 100 | 100* 100** | 100 | 60 | 100 | 100 |
| 1,5-bis(p-Chlorophenyl)-1,4-pentadien-3-one, 4,4-dimethyl-2-imidazolin-2-ylhydrazone, hydrochloride | 0 | | | 50 R | 0 R | | 100 | 100 | 80 | 100* 100** | 80 | 0 | 100 | 100 |
| 1,5-bis(p-Chlorophenyl)-1,4-pentadien-3-one, 4,5,6,7-tetrahydro-1H-1,3-diazepin-2-ylhydrazone | 0 | | | 50 R | 0 | | 100 | 100 | 70 | 100* 100** | 90 | 0 | 90 | 10 |
| 1,5-bis(p-Chlorophenyl)-1,4-pentadien-3-one, (3a,4,5,6,7,7a-hexahydro-2-benzimidazolyl)hydrazone, hydrochloride | 0 | | | 0 | | | 100 | 90 | 0 | 100* 60** | 0 | | 70 | 0 |
| 1,5-bis(p-Chlorophenyl)-1,4-pentadien-3-one, (3a,4,5,6,7,7a-hexahydro-2-benzimidazolyl)hydrazone | 0 | | | 100 | 0 R | 0 | 100 | 100 | 50 | 100* 100** | 80 | 0 R | 100 | 50 |
| 1,4-pentadien-3-one, 1,5-bis-(α,α,α-trifluoro-p-tolyl)-, (1,4,5,6-tetrahydro-5,5-dimethyl-2-pyrimidinyl)hydrazone | 0 | | | 100 | 100 | 0 | 100 100 | 40 | | 100* 70** | 100 | 90 100 | 100 | 100 |
| 1,4-pentadien-3-one, 1,5-bis (α,α,α-trifluoro-p-tolyl)-,4,5,6,7-tetrahydro-1-H-1,3-diazepin-2-yl hydrazone, hydriodide | 0 | | | 100 | 100 | 0 | 100 100 | 80 60 | | 100* 100* 0 | 100 | 90 80 | 100 | 100 |
| 1,4-pentadien-3-one, 1,5-bis[p-(methylthio)-phenyl]-,(4,5,6,7-tetrahydro-1H-1,3- | | | | 0 | | | 100 80 | | | 40* 0 | 0 | | 0 | |

TABLE I-continued
Evaluation of Pentadienone Hydrazones as Insecticides

| | PERCENT MORTALITY | | | | | | | | | | | | |
|---|---|---|---|---|---|---|---|---|---|---|---|---|---|
| | Budworm | | | | | | Armyworms | | | | Tobacco Budworm | | Cabbage Looper | |
| | Eggs | | | Larvae | | | | | | | | | | |
| Compound | 300 ppm | 100 ppm | 10 ppm | 300 ppm | 100 ppm | 10 ppm | 1000 ppm | 100 ppm | 10 ppm | 7 Days | 1000 ppm | 100 ppm | 1000 ppm | 100 ppm |
| diazepin-2-yl) hydrazone | | | | | | | | | | | | | | |

*1000 ppm.
**100 ppm.
R = Reduced feeding

Red imported Fire ants - *Solenopsis invicta* Buren) obtained out-of-doors under natural conditions were used in the imported fire ant screen. Approximately 0.5 cu. ft. of an active ant mound was placed in a plastic tub (13 × 13 × 8) and aged in the laboratory for 3 days before use. The top 3 inches on the inside of the tub were dusted with talc to prevent the ants from escaping. Water was added to the mounds as needed both before and after treatment to help keep them from becoming too dry. The compounds were dispersed in soybean oil starting at a low concentration of approximately 0.05%. The concentration was increased at various increments to approximately 1.0%. Low concentrations were used first to determine if the compound was palatable to the ants. Approximately 7.5 grams of soybean oil containing the toxicant were poured over a small wad of absorbent cotton in a 3-oz. Dixie ® cup. The side of the Dixie cup was placed on top of the mound. Usually 3 tubs were used per concentration. Mortality counts and/or ratings were made at 6 weeks after treatment or longer is warranted. The temperature of the holding rooms was approximately 26° C. with a relative humidity of approximately 50%.

Data obtained are reported in Table II below.

TABLE II
STRUCTURES AND NAMES 1,4-Pentadiene-3-one, 1,5-bis)α,α,α-trifluoro-p-tolyl)-, (1,4,5,6-Tetrahydro-5,5-dimethyl-2-pyrimidinyl)hydrazone

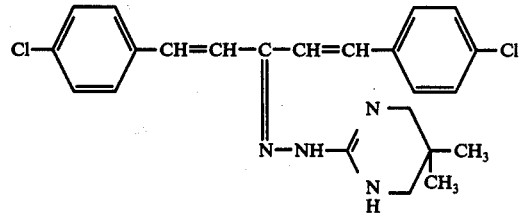

1,4-Pentadien-3-one, 1,5-bis(p-chlorophenyl)-, (3a,4,5,6,7,7a-hexahydro-2-benzimidazolyl)hydrazone, Isomer B

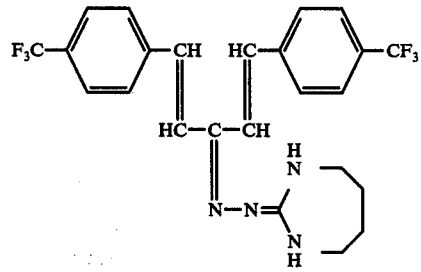

1,4-Pentadien-3-one, 1,5-bis(p-chlorophenyl)-, (1,4,5,6-tetrahydro-5,5-dimethyl-2-pyrimidinyl)hydrazone CA

TABLE II-continued
STRUCTURES AND NAMES 1,4-Pentadien-3-one, 1,5-bis(α,α,α-trifluoro-p-tolyl)-, (E,E)-, azine with hexahydro-2H-1,3-diazepin-2-one CA

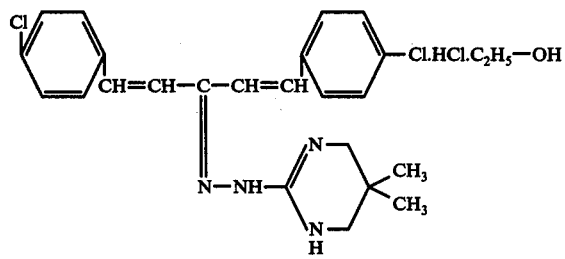

1,4-Pentadien-3-one, 1,5-bis(p-chlorophenyl)-, (1,4,5,6-tetrahydro-5,5-dimethyl-2-pyrimidinyl)hydrazone hydrochloride, compound with ethanol 1,4-Pentadien-3-one, 1,5-bis(p-chlorophenyl)-, (3a,4,5,6,7,7a-hexahydro-2-benzimidazolyl)hydrazone, hydrochloride CA

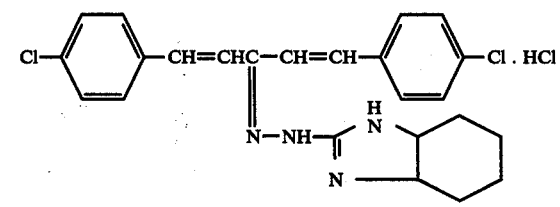

1,4-Pentadien-3-one, 1,5-bis(α,α,α-trifluoro-p-tolyl)-, (E,E)-, azine with hexahydro-2H-1,3-diazepin-2-one-, hydrochloride

TABLE II-continued
STRUCTURES AND NAMES

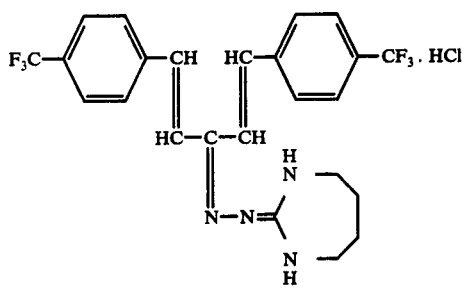

Guanidine, 1-{[p-chloro-α-(p-chlorostyryl)cinnamylidene]-amino}-2,3-diisopropyl, hydriodide

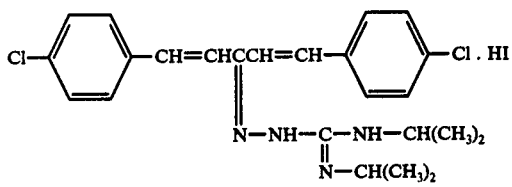

TABLE II-continued
STRUCTURES AND NAMES 1,4-Pentadien-3-one, 1,5-bis(p-chlorophenyl)-5-methyl-2-imidazolin-2-ylhydrazone, hydrochloride

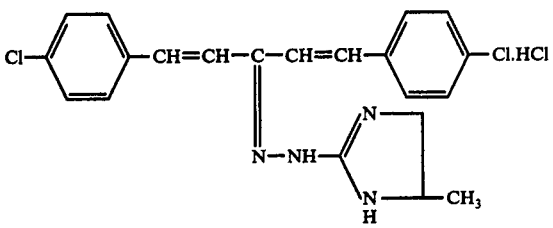

1,4-Pentadien-3-one, 1,5-bis(p-chlorophenyl)-,(4-phenyl-2-imidazolin-2-yl)-hydrazone CA

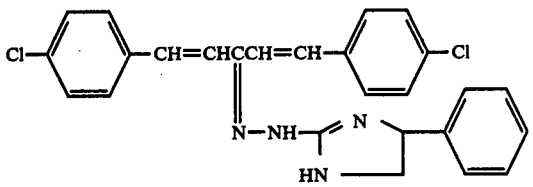

TABLE III
Evaluation of Pentadienone Hydrazones for the Control of the Imported Fire Ant. Three Ant Colonies, Each Concentration

| Structure | % Conc. | Bait Acceptance | 6-Week Results No. colonies alive or dead | Remarks |
|---|---|---|---|---|
| (CF₃-Ph-CH=CH-)₂C=N-NH-[5,5-dimethyl tetrahydropyrimidin-2-yl] | .05<br>1.0 | Fair to Excellent | All 3 dead | Only majors alive in 2 mounds at 3 weeks |
| (Cl-Ph-CH=CH-)₂C=N-NH-[benzimidazoline fused cyclohexane] | .1<br>.2<br>.3<br>.3<br>.4<br>.5 | Excellent<br>Excellent<br>Excellent<br>Excellent<br>Excellent<br>Excellent | All 3 alive<br>All 3 alive<br>All 3 dead<br>Killed 2 of 3<br>Killed 2 of 3<br>All 3 dead | <br><br><br>Only a few alive after 12 weeks.<br>A few majors in one. |
| (Cl-Ph-CH=CH-)₂C=N-NH-[5,5-dimethyl tetrahydropyrimidin-2-yl] | .3<br>3.0 | Excellent<br>Fair to Excellent | Killed 1 of 3<br>All 7 dead at 5 weeks | All dead at 10 weeks.<br>4 dead at 3 weeks. |
| (CF₃-Ph-CH=CH-)₂C=N-NH-[tetrahydropyrimidin-2-yl] | .3 | Excellent | All 3 alive | 2 dead at 10 weeks. |
| (Cl-Ph-CH=CH-)₂C=N-NH-[5,5-dimethyl tetrahydropyrimidin-2-yl] . HCl . EtOH | .5 | Fair to Excellent | All 5 dead | |

TABLE III-continued
Evaluation of Pentadienone Hydrazones for the Control of the Imported Fire Ant. Three Ant Colonies, Each Concentration

| Structure | % Conc. | Bait Acceptance | 6-Week Results No. colonies alive or dead | Remarks |
|---|---|---|---|---|
| (Cl—C₆H₄—CH=CH—)₂C=N—NH—C(=N)(NH)—(tetrahydro ring) · HCl | .3 | Excellent | Killed 2 of 3 | A few alive in one. |
| (CF₃—C₆H₄—CH=CH—)₂C=N—NH—C(=N)(NH)—(tetrahydro ring) · HCl | .3 | Excellent | Killed 1 of 3 | |
| (Cl—C₆H₄—CH=CH—)₂C=N—NH—C(=N—CH(CH₃)₂)(NH—CH(CH₃)₂) · HI | 1.0 | Fair to Good | All 3 alive | Only a few alive in two. |
| (Cl—C₆H₄—CH=CH—)₂C=N—NH—C(=N)(N—CH₃)(imidazoline) · HCl | .3<br>1.0 | Excellent<br>Excellent | All 3 alive<br>1 of 2 colonies killed | |
| (Cl—C₆H₄—CH=CH—)₂C=N—NH—C(=N)(NH)(phenyl-imidazoline) | 2.0<br>0.5 | Poor to Fair | All 3 alive<br>3 of 3 colonies killed | |

EXAMPLE II

The insecticidal activity of the compounds of this invention is further demonstrated by the following tests, wherein pentadienone hydrazones are evaluated as stomach poisons against test insect species at rates of from 30 to 1000 ppm. Test formulations and evaluation procedures are as follows:

Test I. German cockroaches (*Blattella germanica* (Linnaeus)).

A. 11.0 mg of 1,5-bis(α,α,α-trifluoro-p-tolyl)-1,4-pentadien-3-one, 4,5,6,7-tetrahydro-1H-1,3-diazepin-2-ylhydrazone were placed in 11.0 g of creamy peanut butter and thoroughly mixed. This is equivalent to a concentration of approximately 0.1% or 1000 ppm.

B. 1.0 g of A was added to 9.0 g of peanut butter and thoroughly mixed. This is equivalent of 0.01% or 100 ppm.

C. 5.0 g of peanut butter served as the control. Approximately 5.0 g of bait were placed in a 3 cm × 1 cm high plastic cup. The plastic cup of bait and a water wick were placed in a cage 8 inches in diameter and 2.5 inches high. The bottom of the cage was an 8-inch diameter plate of glass resting on a half inch rim which extended inward from the stainless steel side. Twenty adult male German cockroaches were placed in each cage. The cage was covered with a 16-mesh copper wire screen lid. The cages were held at approximately 27° C.

Results are in the following table:

| Compound | Concentration ppm | Percent Mortality | |
|---|---|---|---|
| | | Days Posttreatment 7 | 14 |
| (CF₃—C₆H₄—CH=CH)₂—C(=N—NH—diazepine ring) | 1000<br>100 | 75%<br>5% | 100%<br>5% |
| Control | — | 0% | 0% |

Test II. House flies (*Musca domestica* Linnaeus)

1. 400 g of sugar and 400 g of powdered milk were thoroughly mixed in a gallon ice cream carton.
   A. 222.2 mg of 1,5-bis($\alpha,\alpha,\alpha$-trifluoro-p-)-1,4-pentadien-3-one, 4,5,6,7-tetrahydro-1H-1,3-diazepin-2-ylhydrazone 90% pure were added to 200.0 g of No. 1 and thoroughly mixed. This is equivalent to a concentration of 0.1% or 1000 ppm.
   B. 30.0 g of A were added to 70 g of No. 1 and mixed well. Concentration = 0.03% or 300 ppm.
   C. 10.0 g of A were added to 90 g of No. 1 and mixed well. Concentration = 0.01% or 100 ppm.
   D. 3.0 g of A were added to 97 g of No. 1 and mixed well. Concentration = 0.003% or 30% ppm.
   E. Control was No. 1 only.

Fifty grams of dry bait in a 9.0 cm petri dish bottom were placed in each house fly cage. Each cage, 12 × 12 × 12 inches was made of 16-mesh copper wire screen supported by a wooden frame. One hundred house fly pupae and a water wick were placed in each cage. The cages were held at 28°±2° C. The flies emerged in 2-3 days. Results are in the following table.

| Compound | Concentration ppm | Percent Mortality of Adult House Flies | |
|---|---|---|---|
| | | Days 3-4 | Posttreatment 9-10 |
| 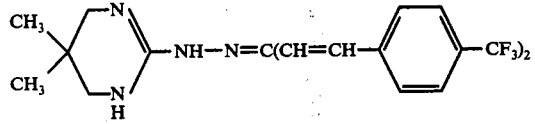 | 1000 | 100 | 100 |
| | 300 | 98.4 | 100 |
| | 100 | 31.7 | 97.6 |
| | 30 | 6.7 | 6.7 |
| Control | — | 1.9 | 5.6 |

Preparation of
1,5-Bis($\alpha,\alpha,\alpha$-trifluoro-p-tolyl)-1,4-pentadiene-3-one
(1,4,5,6-tetrahydro-5,5-dimethyl-2-pyrimidinyl)-hydrazone.

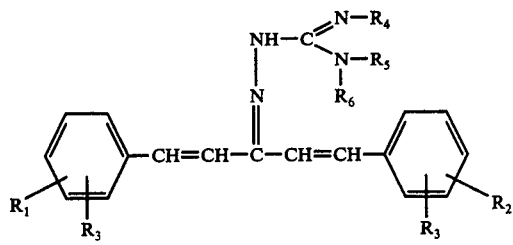

To a mixture of 2.1 g of 5,5-dimethyl-1,4,5,6,-tetrahydropyridinium-2-ylhydrazine hydroiodide and 3.2 g of 1,5-bis($\alpha,\alpha,\alpha$-trifluoro-p-tolyl)-1,4-pentadiene-3-one in 6 ml of absolute ethanol was added one drop of 47% hydriodic acid. The mixture was heated at reflux for 2 to 3 hours and then cooled in ice. The yellow hydroiodide salt which precipitated was collected by filtration and washed with ethanol. The hydroiodide salt was neutralized by stirring with 15 ml of ethyl acetate and 15 ml of saturated sodium carbonate solution. The ethyl acetate mixture was separated from the aqueous phase, dried over magnesium sulfate, and concentrated to give a red oil. The oil was mixed with a little ether, and the mixture refrigerated. The resulting solids were collected and washed with ether and amounted to 1.2 g, melting point 163.5°-164.5° C. Analysis calculated for $C_{25}H_{24}F_6N_4$: C, 60.72; H, 4.89; N, 11.33. Found: C, 60.54; H, 4.73; N, 10.43. The product exists in different crystalline forms, and when recrystallized from isopropyl alcohol, has a melting point of 189°-191° C.

I claim:

1. A method for controlling insects comprising, contacting the insect, or their habitat, with an insecticidally effective amount of a compound having the structure:

[structure diagram]

wherein $R_1$ and $R_2$ each represent hydrogen, halogen, $CF_3$, $C_1$-$C_4$ alkyl, $C_1$-$C_3$ alkoxy or $C_1$-$C_4$ alkylthio; $R_3$ is hydrogen or methyl, provided that when $R_3$ is methyl, $R_1$ and $R_2$ are also methyl; $R_4$ and $R_5$ represent hydrogen or $C_1$-$C_4$ alkyl, and when taken together, an alkylene group of 2 to 6 carbon atoms, a methyl substituted or a phenyl substituted alkylene group of 2 to 4 carbon atoms, a dimethyl substituted alkylene group of 2 to 4 carbon atoms or 1,2-cyclohexylene; and $R_6$ is hydrogen or $C_1$-$C_4$ alkyl; or salts thereof.

2. The method according to claim 1, wherein $R_1$ and $R_2$ each represent H, Cl, Br, $CF_3$, $C_1$-$C_3$ alkyl, methoxy or methylthio; $R_3$ is hydrogen; $R_4$ and $R_5$ each represent hydrogen or $C_1$-$C_3$ alkyl, and when taken together, $C_2$-$C_6$ alkylene, or methyl, dimethyl or phenyl $C_2$-$C_4$ alkylene; and $R_6$ is hydrogen; or the acid addition salts thereof.

3. The method according to claim 2, wherein $R_1$ and $R_2$ are each p-chloro or p-$CF_3$; $R_3$ and $R_6$ are each hydrogen; and $R_4$ and $R_5$ are taken together and are $C_2$-$C_6$ alkylene.

4. The method according to claim 1, wherein the insects are Lepidopterous, Orthopterous, Dipterous or Hymenopterous insects, and the compound is applied at the rate of from 0.28 kg/hectare to 11.2 kg/hectare.

5. The method according to claim 1, wherein the compound is 1,5-bis($\alpha,\alpha,\alpha$-trifluoro-p-tolyl)-1,4-pentadien-3-one, (1,4,5,6-tetrahydro-5,5-dimethyl-2-pyrimidinyl)hydrazone.

6. The method according to claim 1, wherein the compound is 1,5-bis($\alpha,\alpha,\alpha$-trifluoro-p-tolyl)-1,4-pentadien-3-one 4,5,6,7-tetrahydro-1H-1,3-diazepin-2-ylhydrazone, or the acid addition salt thereof.

7. The method according to claim 1, wherein the compound is 1,5-bis(p-chlorophenyl)-1,4-pentadien-3-one 4-phenyl-2-imidazolin-2-ylhydrazone, or the acid addition salt thereof.

8. The method according to claim 1, wherein the compound is 1,5-bis(p-chlorophenyl)-1,4-pentadien- 3-one 4,5,6,7-tetrahydro-1H-1,3-diazepin-2-ylhydrazone, or the acid addition salts thereof.

9. The method according to claim 1, wherein the compound is 1,5-bis(p-chlorophenyl)-1,4-pentadien-3-one (3α, 4,5,6,7,7α-hexahydro-2-benzimidazolyl)hydrazone, or the acid addition salts thereof.

10. The method according to claim 1, wherein the compound is 1,5-bis(p-chlorophenyl)-1,4-pentadien-3-one 1,4,5,6,-tetrahydro-5,5-dimethyl-2-pyrimidinylhydrazone or the acid addition salt thereof with ethanol.

11. The method according to claim 1, wherein the compound is 1,5-bis(p-chlorophenyl)-1,4-pentadien-3-one 4,4-dimethyl-2-imidazolin-2-ylhydrazone or the acid addition salt thereof.

12. A method for protecting agronomic crops, trees, shrubs and ornamentals, from attack by insects comprising, applying thereto an insecticidally effective amount of a compound represented by the formula:

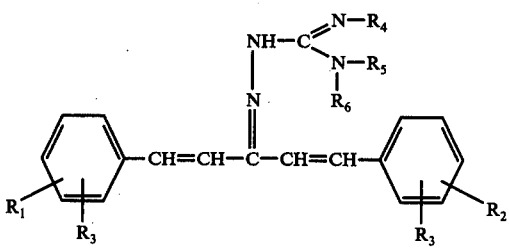

wherein $R_1$ and $R_2$ each represent hydrogen, halogen, $CF_3$, $C_1$–$C_4$ alkyl, $C_1$–$C_4$ alkoxy or $C_1$–$C_4$ alkylthio; $R_3$ is hydrogen or methyl, provided that when $R_3$ is methyl, $R_1$ and $R_2$ are also methyl; $R_4$ and $R_5$ represent hydrogen or $C_1$–$C_4$ alkyl, and when taken together, an alkylene group of 2 to 6 carbon atoms, methyl or a phenyl alkylene group of 2 to 4 carbon atoms, or a dimethyl alkylene group of 2 to 4 carbon atoms; and $R_6$ is hydrogen or $C_1$–$C_4$ alkyl; or salts thereof.

13. The method according to claim 12, wherein the crops are protected from attack by Lepidopterous insects by applying to the crops a compound according to claim 12, wherein $R_1$ and $R_2$ each represent H, Cl, Br, $CF_3$, $C_1$–$C_3$ alkyl, methoxy or methylthio; $R_3$ is hydrogen; $R_4$ and $R_5$ each represent hydrogen or $C_1$–$C_3$ alkyl, and when taken together, $C_2$–$C_6$ alkylene, or methyl, dimethyl or phenyl $C_2$–$C_4$ alkylene; $R_6$ is hydrogen; or the acid addition salts thereof; at the rate of from 0.28 kg/hectare to 11.2 kg/hectare.

14. The method according to claim 1 wherein the compound is 1,5-bis(p-chlorophenyl)-1,4-pentadien-3-one (3α,4,5,6,7,7α-hexahydro-2-benzimidazolyl)hydrazone, hydrochloride.

15. The method according to claim 1, wherein the compound is 1,5-bis(p-chlorophenyl)-1,4-pentadien-3-one (3α,4,5,6,7,7α-hexahydro-2-benzimidazol)hydrazone hydrobromide.

16. The method according to claim 1, wherein the insects are Hymenopterous insects and the compound is applied at the rate of 0.56 to 11.2 kg/hectare.

17. The method according to claim 16, wherein the compound is 1,4-pentadien-3-one, 1,5-bis(α,α,α-trifluoro-p-tolyl)-, (1,4,5,6,-tetrahydro-5,5-dimethyl-2-pyrimidinyl) hydrazone, or the acid addition salt thereof.

18. The method according to claim 16, wherein the compound is 1,5-bis(α,α,α-trifluoro-p-tolyl)-1,4-pentadien-3-one, 4,5,6,7-tetrahydro-1H-1,3-diazepin-2-ylhydrazone, or the acid addition salt thereof.

19. The method according to claim 16, wherein the compound is 1,5-bis(p-chlorophenyl)-1,4-pentadien-3-one(3α, 4,5,6,7,7α-hexahydro-2-benzimidazolyl)hydrazone, or the acid addition salt thereof.

20. The method according to claim 16, wherein the compound is 1,5-bis(α,α,α-trifluoro-p-tolyl)-1,4-pentadien-3-one(E,E)-, azine with hexahydro-2H-1,3-diazepin-2-one, or the acid addition salt thereof.

21. The method according to claim 16, wherein the compound is 1,4-pentadien-3-one, 1,5-bis(p-chlorophenyl)-,5-methyl-2-imidazolin-2-ylhydrazone, hydrochloride, or the acid addition salt thereof.

22. The method according to claim 16, wherein the compound is 1,4-pentadien-3-one, 1,5-bis(p-chlorophenyl)-,(4-phenyl-2-imidazolin-2-yl)-hydrazone, or the acid addition salt thereof.

23. The method according to claim 16, wherein the compound is 1,5-bis(p-chlorophenyl)-1,4-pentadien-3-one (1,4,5,6-tetrahydro-5,5-dimethyl-2-pyrimidinyl)-hydrazone, or the acid addition salt thereof.

24. The method according to claim 17, wherein the insects are ants.

25. The method for protecting crops according to claim 13 wherein the crop is cotton and the compound is 1,4-pentadien-3-one, 1,5-bis(α,α,α-trifluoro-p-tolyl)-,(1,4,5,6,-tetrahydro-5,5-dimethyl-2-pyrimidinyl)hydrazone.

* * * * *